United States Patent [19]
Kayser

[11] Patent Number: 5,497,408
[45] Date of Patent: Mar. 5, 1996

[54] X-RAY EXAMINATION APPARATUS

[75] Inventor: Harald Kayser, Hamburg, Germany

[73] Assignee: U.S. Philips Corporation, New York, N.Y.

[21] Appl. No.: 323,206

[22] Filed: Oct. 14, 1994

[30] Foreign Application Priority Data

Oct. 16, 1993 [DE] Germany ............ 43 35 306.1

[51] Int. Cl.⁶ .................................................. A61B 6/02
[52] U.S. Cl. ......................................... 378/196; 378/197
[58] Field of Search .................................. 378/193, 195, 378/196, 197, 167, 177, 181

[56] References Cited

U.S. PATENT DOCUMENTS

| | | | |
|---|---|---|---|
| 2,504,687 | 4/1950 | Hollstein | 378/196 X |
| 2,997,585 | 8/1961 | Schiring | 378/196 X |
| 3,838,287 | 9/1974 | Barrett et al. | 378/196 X |
| 4,602,378 | 7/1986 | Kelman et al. | 378/26 |
| 4,630,296 | 12/1986 | Haaker et al. | 378/2 |
| 4,630,796 | 12/1986 | Kayser et al. | 248/648 |
| 4,989,228 | 1/1991 | Louiday | 378/196 |

FOREIGN PATENT DOCUMENTS

| | | | |
|---|---|---|---|
| 0160340 | 11/1985 | European Pat. Off. | |
| 836698 | 4/1952 | Germany | |
| 0665730 | 1/1952 | United Kingdom | 378/196 |

*Primary Examiner*—David P. Porta
*Attorney, Agent, or Firm*—Jack D. Slobod

[57] ABSTRACT

An X-ray examination apparatus, including a patient table which is pivotable about a first axis, a spot film device which is arranged over the table top of the patient table and which is displaceable parallel to the table top by means of a transport device, and also an X-ray source which is coupled to the transport device in order to form an X-ray beam. The use of the X-ray source, either underneath the table top for use with the spot film device, or over the table top for overtable X-ray exposures, positioning is possible in that the X-ray source is pivotable about a second axis which is connected to the transport device and which extends parallel to the first axis.

3 Claims, 2 Drawing Sheets

X-RAY EXAMINATION APPARATUS

BACKGROUND OF THE INVENTION

1. Field of the Invention

The invention relates to an X-ray examination apparatus, including a patient table which is pivotable about a first axis, a spot film device which is arranged over the table top of the patient table and which can be displaced parallel to the table top by means of a transport device, and also an X-ray source which is coupled to the transport device.

2. Description of the Related Art

An X-ray examination apparatus of this kind is known from EP-OS 160 340 which corresponds to U.S. Pat. No. 4,630,796. Such an X-ray examination apparatus enables the radiologist to perform X-ray fluoroscopy of a patient and to make X-ray images. During the X-ray exposures, with the patient table in the horizontal position, the X-ray source is situated underneath the patient table and the X-ray detector device in the spot film device is situated over the table. However, X-ray examination apparatus of this kind can also be used to form, by means of a second X-ray tube which is situated over the patient table, X-ray images on a film which is present in a moving grid device which is arranged underneath the table top in the X-ray examination apparatus. These X-ray images are also referred to as "overtable X-ray images". Thus, a further diagnostic station is realised without an additional X-ray generator and a table being required.

SUMMARY OF THE INVENTION

It is an object of the present invention to construct an X-ray examination apparatus of the kind set forth in such a manner that the expenditure in components for producing the overtable X-ray images is even further reduced. This object is achieved in accordance with the invention in that the X-ray source is pivotable about a second axis which is connected to the transport device, or to a part rigidly connected thereto, and which extends parallel to the plane of the table top and preferably parallel to the first axis.

In an X-ray examination apparatus in accordance with the invention, the X-ray source can be pivoted upwards from its normal position, in which it is centered on the X-ray spot film device, about the second axis so that overtable X-ray images can be formed in conjunction with a moving grid device situated underneath the table top; the X-ray spot film device then remains over the patient table.

The X-ray examination apparatus in accordance with the invention thus enables the formation of overtable X-ray images without requiring a second X-ray source and associated components, such as a stand, high-voltage cable, multi-leaf diaphragm etc. In principle the second axis could also extend parallel to the longitudinal direction of the table top; however, it preferably extends parallel to the first axis.

In a preferred embodiment of the invention, the focus of the X-ray source and the centre of the X-ray spot film device are situated in a plane extending perpendicularly to the longitudinal direction of the table top, the second axis being situated at a distance from this plane. As is customary in X-ray examination apparatus of the kind set forth, the focus of the X-ray source and the centre of the X-ray spot film device are again situated in a plane perpendicular to the longitudinal direction of the table top, but the second axis is now situated outside the plane. Therefore, after pivoting through 180°, the X-ray source is situated over the table top and has been shifted in the longitudinal direction relative to the X-ray spot film device. Thus, collisions between X-ray source and spot film device are precluded and the spot film device is situated outside the beam path of the X-ray source situated over the table top.

In a further embodiment of the invention, underneath the table top there is provided a moving grid device which is coupled to the movement of the spot film device in the longitudinal direction. It is thus achieved that the moving grid device is situated at a defined distance from the X-ray spot film device in the longitudinal direction of the table top. When the same holds for the X-ray source, the X-ray source in the overtable position and the moving grid device are automatically aligned relative to one another.

In another embodiment of the invention, the X-ray source is pivotable about a third axis which extends parallel to the first and the second axis and through the X-ray source, the X-ray source being coupled to a stationary point on the X-ray apparatus by way of a coupling rod and there being provided means for motor-drive) displacement of the X-ray source in the longitudinal direction of the patient table. Using few additional means, because the means for the motor-driven displacement usually are present already for other purposes, linear tomography is thus possible.

BRIEF DESCRIPTION OF THE DRAWINGS

The invention will be described in detail hereinafter with reference to the drawing. Therein.

DETAILED DESCRIPTION OF THE PREFERRED EMBODIMENTS

Figure 1:
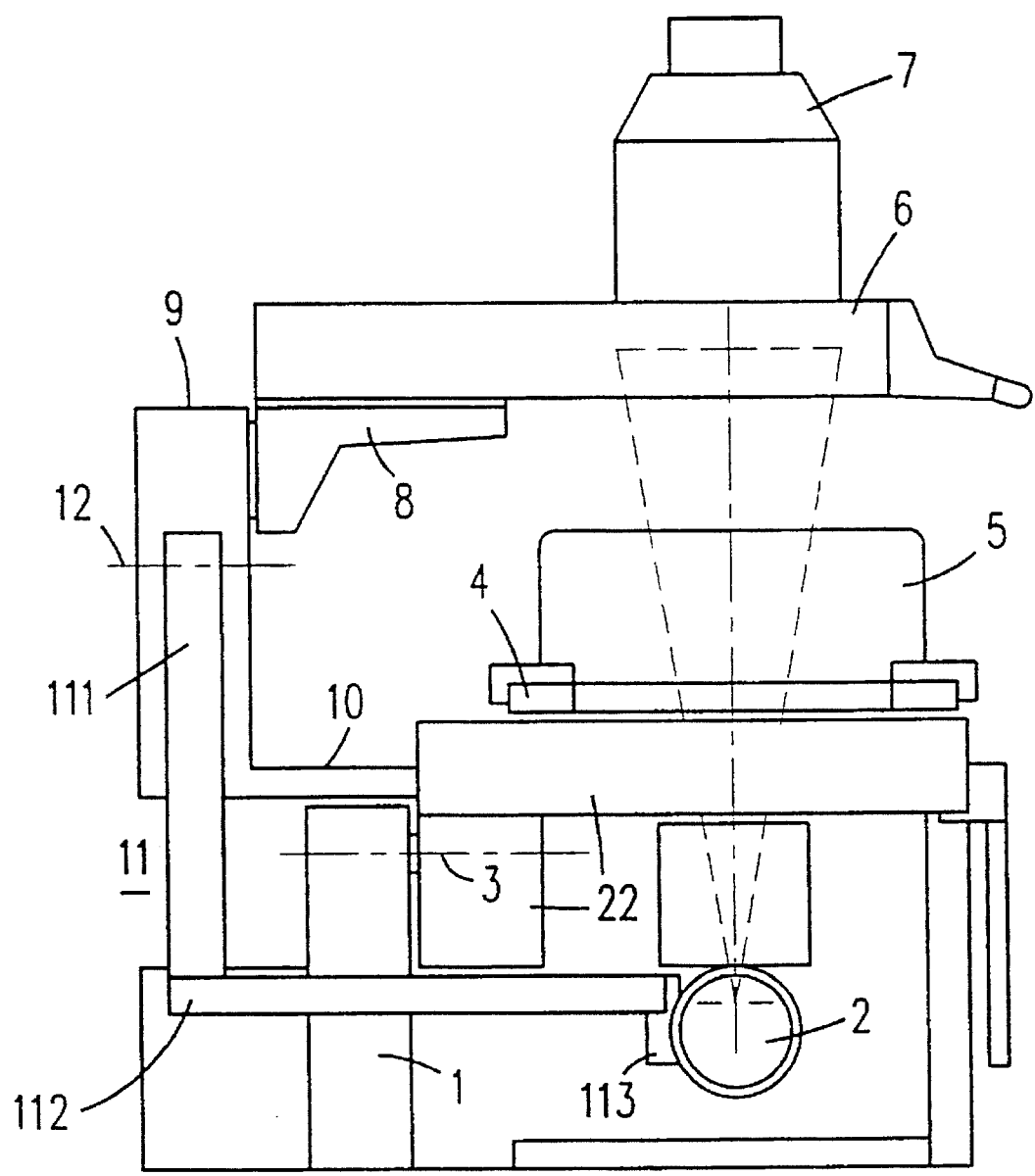
FIG. 1 shows the X-ray examination apparatus in accordance with the invention, viewed from the head end.

The reference numeral 1 in the Figures denotes the base of the X-ray examination apparatus which supports the apparatus and connects it to the floor. A patient table 22 is connected to the base 1 so as to be pivotable about a horizontal axis 3. The patient table comprises a motor-driven table top 4, i.e. a table top which can be displaced in its plane. In the horizontal position of the table top shown in FIG. 2, an X-ray source 2 (FIG. 2) is situated underneath the table top. Over the table top there is situated an X-ray spot film device 6 which usually comprises an image intensifier 7.

In the position of the X-ray source 2 shown in FIG. 1 it is aligned relative to the spot film device 6, i.e. the focus of the X-ray source wherefrom the X-rays emanate and the centre of the entrance screen of the X-ray image intensifier are situated on a straight line extending perpendicularly to the table top 4. This alignment is maintained during pivoting about the axis 3 (the X-ray source 2 and the spot film device 6 are then also pivoted) and also upon displacement of the X-ray spot film device in the longitudinal direction of the table top or in the transverse direction (parallel to the pivot axis 3).

The spot film device 6 is also displaceable in the compression direction, i.e. perpendicularly to the table top 4. To this end, there is provided a compression carriage 8 which is journalled so as to be slidable in the compression direction in a so-called tower 9. The tower 9 itself is supported by a transport device in the form of a carriage 10 which is slidable in the longitudinal and the transverse direction underneath the table top 4. When the spot film device 6 is displaced in the longitudinal direction or the transverse direction, the carriage 10 as well as the X-ray source 2 coupled thereto are also displaced, so that the X-ray source 2 and the spot film device 6 remain centered relative to one another during such a displacement. The X-ray examination apparatus described thus far is already known from the cited EP-OS 160 340.

In accordance with the invention, the X-ray source 2 is not rigidly connected to the tower 9 or the carriage 10, but to a support 11 which is pivotable about an axis 12 which preferably extends over the table top 4, parallel to the axis 3, and which is connected to the tower 9 (or the carriage 10). The support comprises an arm 111, one end of which is pivotable about the axis 12 and the other end of which is connected to an arm 112 which extends in the transverse direction and which itself supports a third arm 113 which extends perpendicularly to the two arms 111, 112 and which is connected to the X-ray source 2. These three arms of the support 11 ensure that the X-ray source 2 and the image intensifier 7 of the X-ray spot film device 6 are centered relative to one another even though the pivot axis 12 does not extend through the plane 13 which is perpendicular to the table top 4 and which contains the focus of the X-ray source and the centre of the entrance screen of the intensifier. As is clearly shown in FIG. 2, the pivot axis 12 is offset in the direction of the head end relative to the plane 13.

In order to prepare the X-ray apparatus for an overtable X-ray exposure, the X-ray tube 2 must be pivoted through 180°. To this end, the X-ray spot film device (and hence also the carriage 10 and the X-ray source 2) are moved to the head end (being the left-hand end in FIG. 2). In this end position a lock which locks the support 11 relative to the pivot axis 12 is released and the support is pivoted 180° upwards about the axis 12, in which position (denoted by solid lines in FIG. 2) it is locked again. This pivotal motion is preferably assisted by suitable means, for example a spring, a gas compression spring or the like, in such a manner that the moment produced by the X-ray source relative to the axis 12 is compensated for. In the overtable position of the X-ray source thus reached (denoted by solid lines in FIG. 2) the distance between the focal spot of the X-ray source 2 and the plane 13 amounts to twice the distance between this plane and the pivot axis 12.

Overtable images can then be recorded on a film situated in a moving grid device 14. The moving grid device is arranged underneath the table top 4 and can be displaced parallel thereto. The alignment of the X-ray source relative to the moving grid device 14 or the film present therein, can be realised in a customary manner by means of a light-beam indicator of the multi-leaf diaphragm connected to the X-ray source 2. Alignment relative to the X-ray source 2, however, can be dispensed with for X-ray exposures with a beam path extending perpendicularly to the table top when the moving grid device is connected to the tower 9 via a coupling device 15 whereby the moving grid device is moved together with the tower 9.

Thus, in the overtable position of the X-ray source 2 it is also possible to form layer images with a linear blurring motion. To this end, there is provided in known manner a coupling rod 16 which is pivotable about an axis 17 which is stationary relative to the table top 4 and which extends parallel to the axes 3 and 12. The two ends of the coupling rod 16 are connected to the X-ray source 2 and to a film cassette, so that these components are moved in opposite directions in response to a pivotal motion of the coupling rod around the axis 17. All parts of the patient which are situated outside a plane which contains the axis 17 and which extends parallel to the table top 4 are reproduced in a blurred manner, a sharp image being formed only of said plane (layer).

Figure 2:
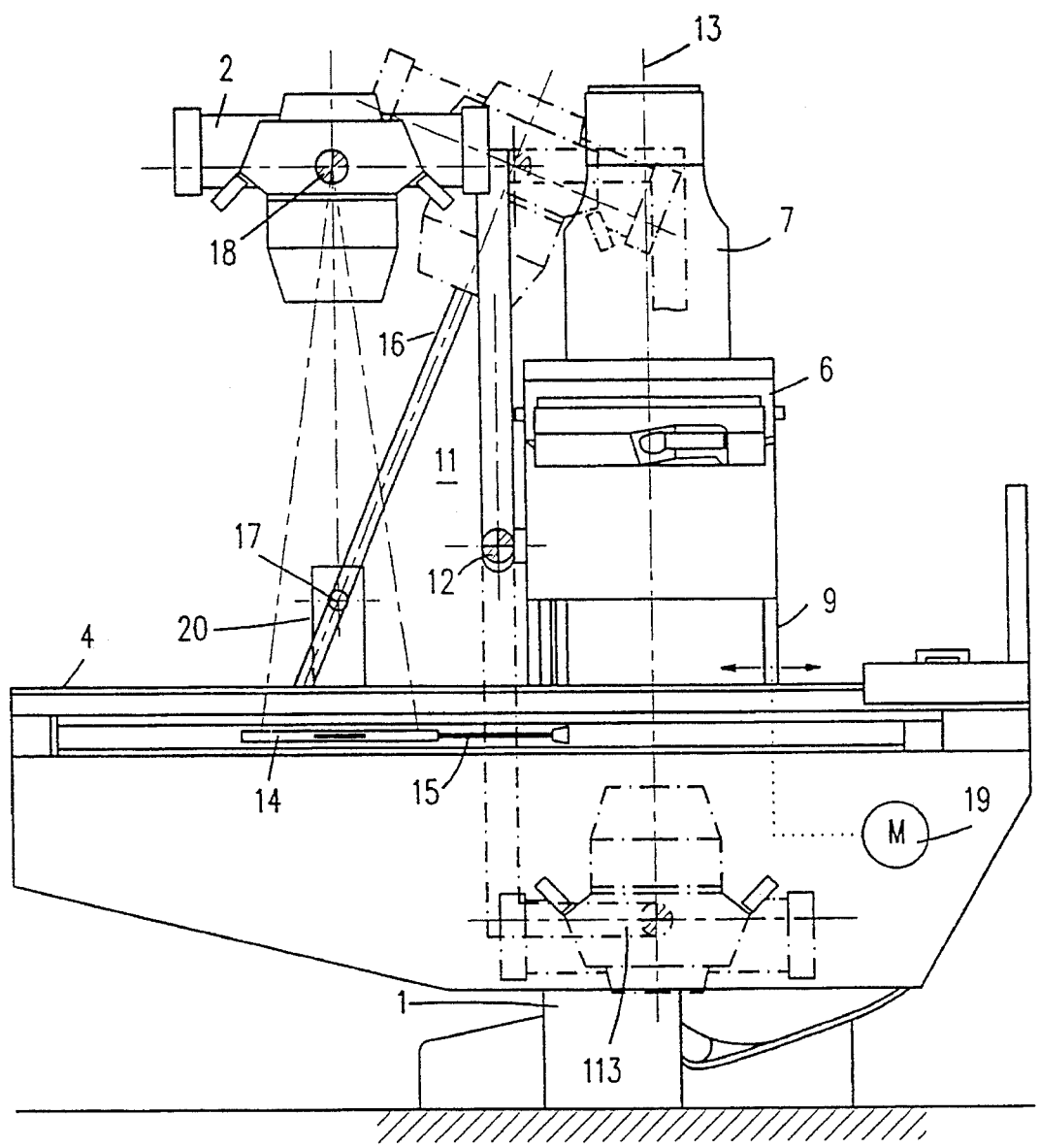
FIG. 2 is a side elevation of the same apparatus.

In order to ensure that in these cases the X-ray source remains aligned relative to the film cassette moved in the opposite direction, it must be pivotable about an axis 18 which extends through the focus of the X-ray source. Dash-dot lines in FIG. 2 show the X-ray source in an overtable position required for a layer image. In order to displace the X-ray source during the layer exposure, there may be provided a motor drive 19 (diagrammatically indicated in FIG. 2) which acts on the tower 9 or the carriage 10 and which displaces it in the longitudinal direction. Such a motor drive is already provided in most X-ray examination apparatus of this kind in order to assist the displacement of the X-ray spot film device and the X-ray source. However, it is alternatively possible to realise the oppositely directed movements of the X-ray source 2 and the film cassette by driving the table top while the supporting part 20, in which the shaft 17 of the coupling rod 16 is journalled, is coupled to the table top. In apparatus of this kind there is usually provided a drive for the table top 4 anyway. However, the patient positioned on the table top 4 is then also moved during the layer exposure. This may cause motional unsharpness.

When the X-ray source is situated to the same side of the table top as the X-ray spot film device 6, further examination techniques can also be carried out. For example, the examination apparatus can be pivoted clock-wise through 90° about the axis 3. When the source 2 is then also rotated through 180°, X-ray images can be formed with a beam path extending horizontally (away from the table top), for example on a moving grid device secured to a wall of the examination room. Moreover, other exposure techniques are possible, for example with an X-ray examination apparatus inclined relative to the horizontal and with X-ray beam extending in the vertical direction for recording on a cassette situated in a horizontal plane, for example for forming X-ray images at the bed of a patient.

I claim:

1. An X-ray examination apparatus, comprising a patient table which is pivotable about a first axis, a spot film device which is arranged over a table top of the patient table, which table top has a longitudinal direction and which spot film device has a center and can be displaced parallel to the table top by means of a transport device, and also comprising an X-ray source which is coupled to the transport device said X-ray source having a focus, wherein the X-ray source is pivotable about a second axis which is connected to the transport device, or to a part rigidly connected thereto, and which extends parallel to the plane of the table top and parallel to the first axis and the focus of the X-ray source and the center of the X-ray spot film device are situated in a plane extending perpendicularly to the longitudinal direction of the table top, the second axis being situated at a distance from this plane.

2. An X-ray examination apparatus as claimed in claim 1, wherein the X-ray source is pivotable about a third axis which extends parallel to the first and second axes and which extends through the X-ray source, the X-ray source being coupled to a stationary point on the X-ray apparatus via a coupling rod, there being provided means for motor-driven displacement of the X-ray source in the longitudinal direction of the patient table.

3. An X-ray examination apparatus as claimed in claim 1, wherein underneath the table top there is provided a moving grid device which can be coupled to the movement of the X-ray spot film device in the longitudinal direction of the patient table.

* * * * *